(12) United States Patent
Schwartz

(10) Patent No.: US 9,423,182 B2
(45) Date of Patent: Aug. 23, 2016

(54) ROLLER HEARTH FURNACE AND METHOD FOR HEATING WORKPIECES

(75) Inventor: Rolf-Josef Schwartz, Simmerath (DE)

(73) Assignee: Schwartz GmbH (DE)

( * ) Notice: Subject to any disclaimer, the term of this patent is extended or adjusted under 35 U.S.C. 154(b) by 192 days.

(21) Appl. No.: 14/006,720

(22) PCT Filed: Mar. 23, 2012

(86) PCT No.: PCT/EP2012/055188
§ 371 (c)(1),
(2), (4) Date: Apr. 15, 2014

(87) PCT Pub. No.: WO2012/130750
PCT Pub. Date: Oct. 4, 2012

(65) Prior Publication Data
US 2014/0227651 A1    Aug. 14, 2014

(30) Foreign Application Priority Data
Mar. 25, 2011   (DE) .......................... 10 2011 006 171

(51) Int. Cl.
*F26B 13/18*    (2006.01)
*F27B 9/30*     (2006.01)
(Continued)

(52) U.S. Cl.
CPC .............. *F27B 9/30* (2013.01); *C21D 9/0012* (2013.01); *C21D 9/0056* (2013.01); *F27B 9/047* (2013.01);
(Continued)

(58) Field of Classification Search
CPC .... F27B 9/2407; F27B 9/2469; F27D 3/026; G03G 15/2053; F26B 13/18
USPC .............. 432/60, 228, 246; 219/469; 492/46
See application file for complete search history.

(56) References Cited

U.S. PATENT DOCUMENTS

| | | | |
|---|---|---|---|
| 3,656,720 A | * | 4/1972 | Westeren ................ F27B 9/045 432/122 |
| 4,154,433 A | * | 5/1979 | Kato ........................ C21D 1/74 266/251 |

(Continued)

FOREIGN PATENT DOCUMENTS

| | | |
|---|---|---|
| JP | 07090352 | 4/1994 |
| JP | 06185876 | 7/1994 |

(Continued)

OTHER PUBLICATIONS

International Search Report PCT/EP2012/055188, completed Jun. 15, 2012; w/information on patent family members.

(Continued)

*Primary Examiner* — Gregory A Wilson
(74) *Attorney, Agent, or Firm* — Tarolli, Sundheim, Covell & Tummino LLP

(57) ABSTRACT

The invention relates to a roller hearth furnace for heating workpieces, comprising at least one furnace chamber for receiving the workpieces, the chamber having at least two lateral furnace walls. At least one transport roller for transporting the workpieces through the furnace chamber is arranged inside the furnace chamber, and each of the furnace walls has at least one opening through which the transport roller can be guided. At least one rolling bearing unit is arranged on each of the outer sides of the furnace walls, said rolling bearing unit being designed to accommodate and support the transport roller outside the furnace chamber. The roller hearth furnace comprises a flushing system for the rolling bearing unit, said flushing system being designed to conduct a flushing gas through the rolling bearing unit, wherein the flushing gas can be conducted from a side of the rolling bearing unit facing away from the furnace wall through the rolling bearing unit and through the opening of the furnace wall into the furnace chamber of the roller hearth furnace. The invention further relates to a method for heating workpieces in such a roller hearth furnace.

9 Claims, 4 Drawing Sheets

Figure 1A:
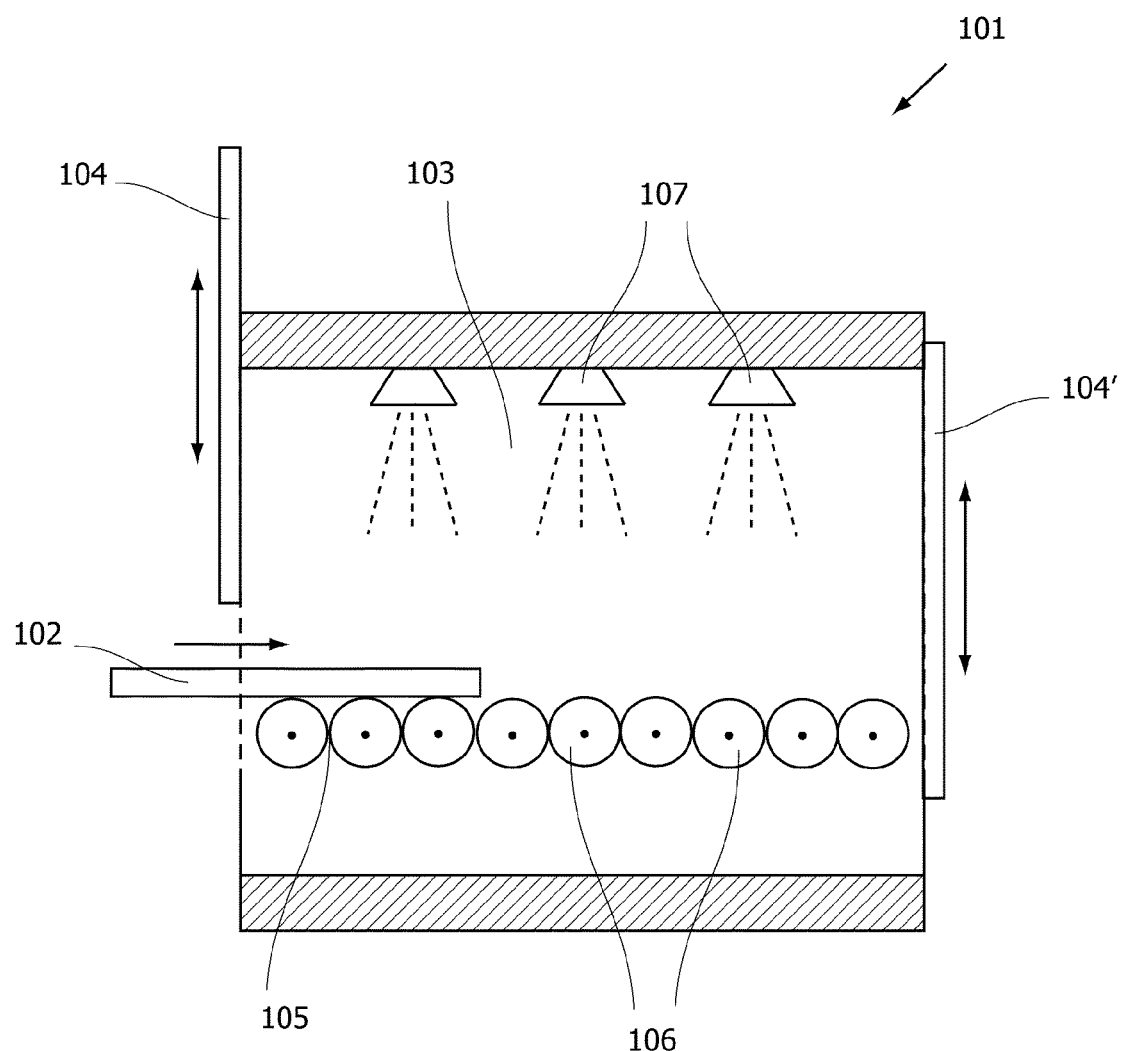

(51) Int. Cl.
  *F27B 9/04* (2006.01)
  *F27B 9/24* (2006.01)
  *F27B 17/00* (2006.01)
  *F27D 3/02* (2006.01)
  *F27D 7/02* (2006.01)
  *F27D 99/00* (2010.01)
  *C21D 9/00* (2006.01)

(52) U.S. Cl.
  CPC ........... *F27B 9/2407* (2013.01); *F27B 9/2469* (2013.01); *F27B 9/3005* (2013.01); *F27B 17/0016* (2013.01); *F27B 17/0083* (2013.01); *F27D 3/026* (2013.01); *F27D 7/02* (2013.01); *F27D 99/0073* (2013.01); *F27D 2007/023* (2013.01)

(56) References Cited

U.S. PATENT DOCUMENTS

| | | | | |
|---|---|---|---|---|
| 5,362,230 A | * | 11/1994 | Facco | F27D 3/026 432/128 |
| 5,370,530 A | * | 12/1994 | Facco | F27D 3/026 138/147 |
| 7,371,296 B1 | * | 5/2008 | Johnston | C21D 1/76 148/516 |
| 7,520,746 B1 | * | 4/2009 | Johnston | F27B 9/10 148/516 |
| 8,714,559 B2 | * | 5/2014 | Hoeting | F16J 15/4478 277/400 |
| 2006/0251999 A1 | | 11/2006 | Wuenning | |

FOREIGN PATENT DOCUMENTS

| | | | |
|---|---|---|---|
| JP | 2000109926 | | 4/2000 |
| JP | 2000109926 A | * | 4/2000 |
| JP | 2009030848 | | 2/2009 |
| JP | 2010043816 | | 2/2010 |

OTHER PUBLICATIONS

Translated International Preliminary Report on Patentability (PCT/EP2012/055188) relating to International Search Report completed Jun. 15, 2012.

* cited by examiner

ROLLER HEARTH FURNACE AND METHOD FOR HEATING WORKPIECES

The invention relates to a roller hearth furnace for heating workpieces. This roller hearth furnace comprises at least one furnace chamber for accommodating the workpieces, said chamber having at least two furnace side walls, whereby at least one transport roller for transporting the workpieces through the furnace chamber is arranged inside the furnace chamber. The furnace walls each have at least one opening through which the transport roller can be guided, and there is at least one roller bearing unit that is arranged on the outside of the furnace walls and that is designed to accommodate and support the transport roller outside of the furnace chamber.

The invention also relates to a method for heating workpieces in which such a roller hearth furnace is employed.

The industrial sector is making increasing use of steel parts that are supposed to have the best possible strength-to-weight ratio. This can be done, for example, by means of the so-called press-hardening or hot-stamping process. In this process, a sheet metal part is heated to about 800° C. to 1000° C. [1472° F. to 1832° F.] and subsequently shaped and quenched in a cooled die. As a result, the strength of the sheet metal part increases as much as three-fold. Press-hardening makes it possible to construct lighter and yet stiffer steel parts by combining heat treatment and shaping with simultaneous controlled cooling. Aside from the press-hardening of steel parts, the industry sector also employs numerous other processes in which it is necessary to heat workpieces in a furnace such as, for instance, when workpieces are annealed or hardened.

When it comes to the heat treatment of steel parts, various furnace concepts have been devised in the past. Especially the principle of a continuous furnace finds widespread use for press hardening. With this furnace principle, the steel parts that are to be heated are transported through the furnace by conveyors. For purposes of heating the steel parts, such continuous furnaces normally have one or more furnace chambers in which furnace gas is present and into which heat generated by heating elements is fed directly or indirectly. The steel parts that are to be heated are transported through the furnace by a conveyor. Rollers in the form of a roller conveyor are very often used as the conveyor.

The rollers of the roller conveyor are each guided on both sides of the continuous furnace through openings in the furnace wall of the furnace chamber and are supported outside of the furnace chamber in roller bearings that are usually configured as ball bearings and that are arranged on the outside of the furnace wall. Since the temperature on the outside of the wall of the furnace chamber is only about 100° C. [212° F.], ball bearings that have lubricants inside can be used, thus improving the running properties of the ball bearings and influencing their service life.

However, during operation of the roller hearth furnace, impurities in the lubricant and/or reductions in the amount of lubricant often shorten the service life of the ball bearings used for the rollers. The reason for this can be, for example, furnace gas that comes out of the roller hearth furnace and escapes from the furnace chamber to the outside through the openings in the furnace wall, a process in which it also flows through the ball bearings arranged on the outside of the furnace wall. Particles that are created in the furnace while the rollers are turning and that stem from the resultant friction against the ceramic insulation wall are partially conveyed by the furnace gas to the outside and are entrained into the ball bearings as they flow through. Moreover, due to the high temperature of the furnace gas, the lubricant slowly disintegrates, so that the amount of lubricant diminishes correspondingly over the course of time.

The impurities in the lubricant caused by the particle entrainment as well as the drop in volume due to the hot furnace gas contribute to increasing the wear and tear of the ball bearings used for the rollers and thus have a detrimental effect on the service life of the ball bearings.

Before this backdrop, one objective of the invention is to put forward a roller hearth furnace for heating workpieces with which the service life of the ball bearings used for the rollers of the roller conveyor is prolonged.

Another objective of the invention is to put forward a method for heating workpieces with which such a roller hearth furnace can be used.

The invention puts forward a roller hearth furnace for heating workpieces, comprising at least one furnace chamber for accommodating the workpieces, said chamber having at least two furnace side walls. At least one transport roller for transporting the workpieces through the furnace chamber is arranged inside the furnace chamber, and the furnace walls each have at least one opening through which the transport roller can be guided. There is at least one roller bearing unit that is arranged on the outside of the furnace walls and that is designed to accommodate and support the transport roller outside of the furnace chamber. The roller hearth furnace has a purging system for the roller bearing unit that is designed to feed a purge gas through the roller bearing unit, whereby the purge gas can be fed from one side of the roller bearing unit facing away from the furnace wall through the roller bearing unit and through the opening in the furnace wall all the way into the furnace chamber of the roller hearth furnace. In this process, the purge gas can be provided at a pressure that is greater than the internal pressure in the furnace chamber of the roller hearth furnace.

Feeding a purge gas from a purging system and passing it through the roller bearing unit entails the advantage that no hot furnace gas from the furnace chamber can flow through the roller bearing unit. Since the furnace gas is provided at a pressure that is greater than the internal pressure that prevails in the furnace chamber, a targeted purge gas flow is generated into the furnace chamber which prevents hot and contaminated furnace gas from the furnace chamber from flowing through the roller bearing unit. On the one hand, this prevents lubricant of the roller bearing unit from being disintegrated by the hot furnace gas. On the other hand, no impurity particles from the furnace chamber are entrained into the roller bearing unit, which could destroy the lubricant. Since, as a result, the composition and quantity of the lubricant are retained over a longer period of time, there is less wear and tear and the service life of the roller bearing unit is prolonged considerably, which means that it can be used for a longer period of time. Owing to the fact that there is less wear and tear, the roller bearing unit does not have to be replaced as often, which translates into a financial advantage for such a roller hearth furnace, thanks to the reduction in costs.

In one embodiment of the roller hearth furnace, the purging system comprises a piping system to feed the purge gas to the roller bearing unit, whereby the piping system is arranged on the outside of the furnace wall of the roller hearth furnace.

Since the temperature on the outside of the furnace wall of the furnace chamber is only about 100° C. [212° F.], the arrangement of the piping system for the purging system on the outside of the furnace wall ensures that the purge gas does not heat up excessively before it is fed to the roller bearing unit. This, in turn, means that the lubricant of the roller bearing unit will not disintegrate.

Moreover, devices that might already be part of the construction of the roller hearth furnace can be used as the piping system. Therefore, in a refinement of the roller hearth furnace, it is provided that a stabilizer of the furnace wall can be employed as the piping system. This eliminates the need to install additional piping systems to feed the purge gas to the roller bearing unit. Consequently, no additional resources in terms of material or assembly are needed in order to install the piping system.

A refinement of the roller hearth furnace is characterized in that the roller bearing unit comprises an inner roller bearing next to which an outer roller bearing is arranged in such a way that the two roller bearings form a pair, whereby the inner roller bearing is situated closer to the outside of the furnace wall of the roller hearth furnace than the outer roller bearing, and in that a cavity is formed between the two roller bearings of the pair of roller bearings.

In one embodiment of the roller hearth furnace, a sealing element is arranged on one side of the outer roller bearing, and this side faces the cavity formed between the two roller bearings.

In a refinement of the roller hearth furnace, the piping system of the purging system is connected to the cavity in such a way that purge gas can be fed into the cavity, whereby the purge gas can then be conveyed out of this cavity through the inner roller bearing and through the opening in the furnace wall all the way into the furnace chamber of the roller hearth furnace.

Since the cavity is formed between the two roller bearings of the pair of roller bearings and since the cavity is connected to the piping system in order to feed the purge gas, it is achieved that the purge gas can flow directly to the inner roller bearing—which is situated closer to the outside of the furnace wall and would thus be exposed to a greater extent to the exiting furnace gas—and can then flow through it. This effect is further intensified in that the sealing element seals off the outer roller bearing against the purge gas in the cavity.

An embodiment of the roller hearth furnace provides that the purging system has a flow-rate meter that is designed to measure the flow rate at which the purge gas can be fed through the roller bearing unit and through the opening in the furnace wall all the way into the furnace chamber of the roller hearth furnace.

The use of a flow-rate meter allows the flow rate and thus the pressure of the purge gas in the purging system to be checked. This turns out to be advantageous since, if the flow rate is too slow, the purge gas could be displaced by furnace gas exiting from the furnace chamber, so that it would not be the purge gas that flows through the roller bearing unit, but rather the hot furnace gas. An excessive flow rate of the purge gas through the roller bearing unit, in turn, could damage it.

A refinement of the roller hearth furnace provides that the purging system comprises a control element that is designed to regulate the flow rate of the purge gas. Consequently, the adjustment capabilities offered by the control element make it possible to respond appropriately to changes in the atmospheric conditions inside the furnace chamber.

In one embodiment of the roller hearth furnace, inert gas can be employed as the purge gas. In another embodiment of the roller hearth furnace, air that can have been purified and/or dried can be used as the purge gas.

The use of different types of gases as the purge gas allows the purging system to be adapted flexibly to the requirements of various types of roller hearth furnaces such as, for example, furnaces with an inert-gas atmosphere or furnaces with an air flow. As a result, the roller hearth furnaces according to the invention are available for different areas of application.

The invention also puts forward a method for heating workpieces in a roller hearth furnace. Here, the roller hearth furnace comprises at least one furnace chamber for accommodating the workpieces, said chamber having at least two furnace side walls, and at least one transport roller for transporting the workpieces through the furnace chamber is arranged inside the furnace chamber. The furnace walls each have at least one opening through which the transport roller is guided, and there is at least one roller bearing unit that is arranged on the outside of the furnace walls and that accommodates and supports the transport roller outside of the furnace chamber. In the method, a purging system feeds a purge gas through the roller bearing unit, whereby the purge gas is fed from one side of the roller bearing unit facing away from the furnace wall through the roller bearing unit and through the furnace wall all the way into the furnace chamber of the roller hearth furnace. In this process, the purge gas is provided at a pressure that is greater than the internal pressure in the furnace chamber of the roller hearth furnace.

The pressure of the purge gas ensures that the purge gas can flow through the roller bearing unit and that the furnace gas is displaced out of the roller bearing unit and out of the opening in the furnace wall.

A refinement of the invention provides that the purge gas is conveyed out of the piping system of the purging system and fed into a cavity, whereby this cavity is formed between an inner roller bearing and an outer roller bearing of the roller bearing unit, and these roller bearings are arranged as a pair of roller bearings next to each other on the outside of the furnace wall of the furnace chamber of the roller hearth furnace in such a manner that the inner roller bearing is closer to the outside of the furnace wall than the outer roller bearing.

The above-mentioned advantages as well as other advantages, special features and practical refinements of the invention are elucidated on the basis of the embodiments that are described below with reference to the figures.

Figure 1B:
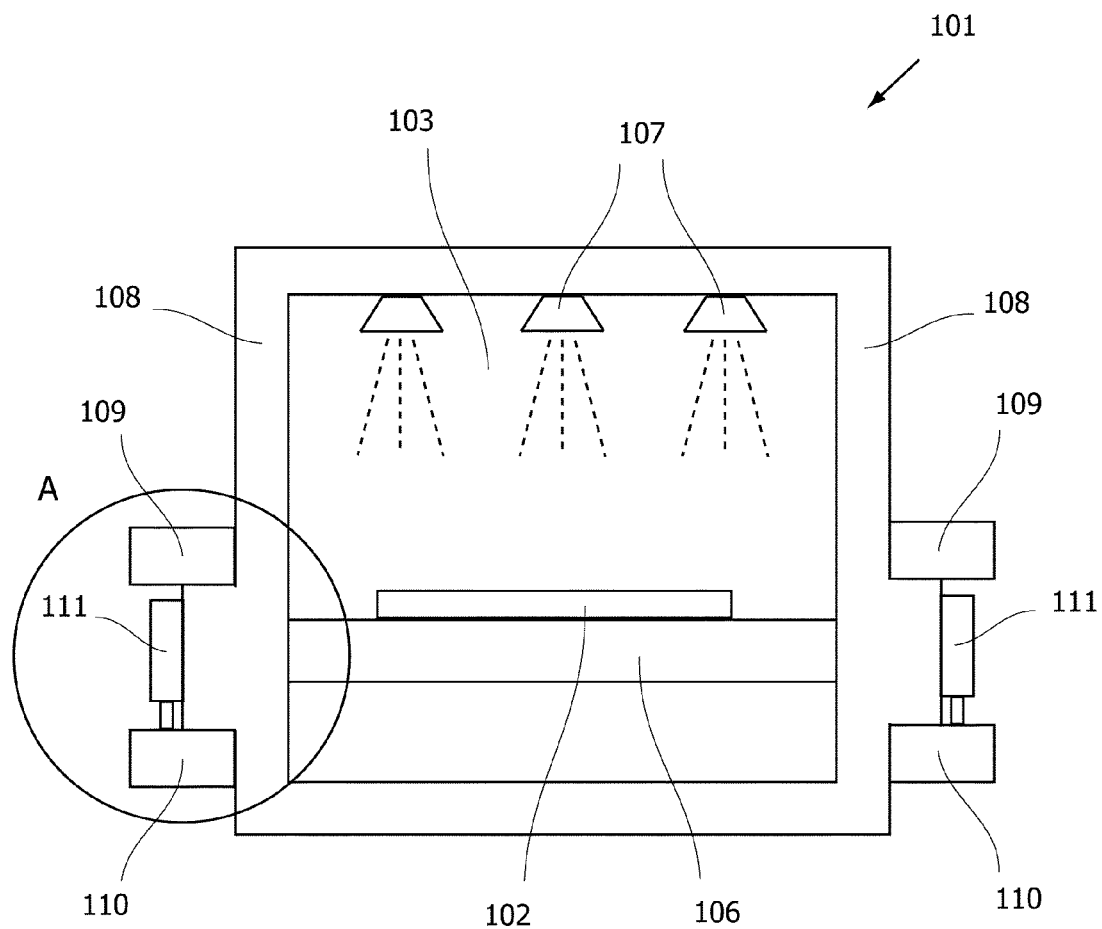
Figure 2A:
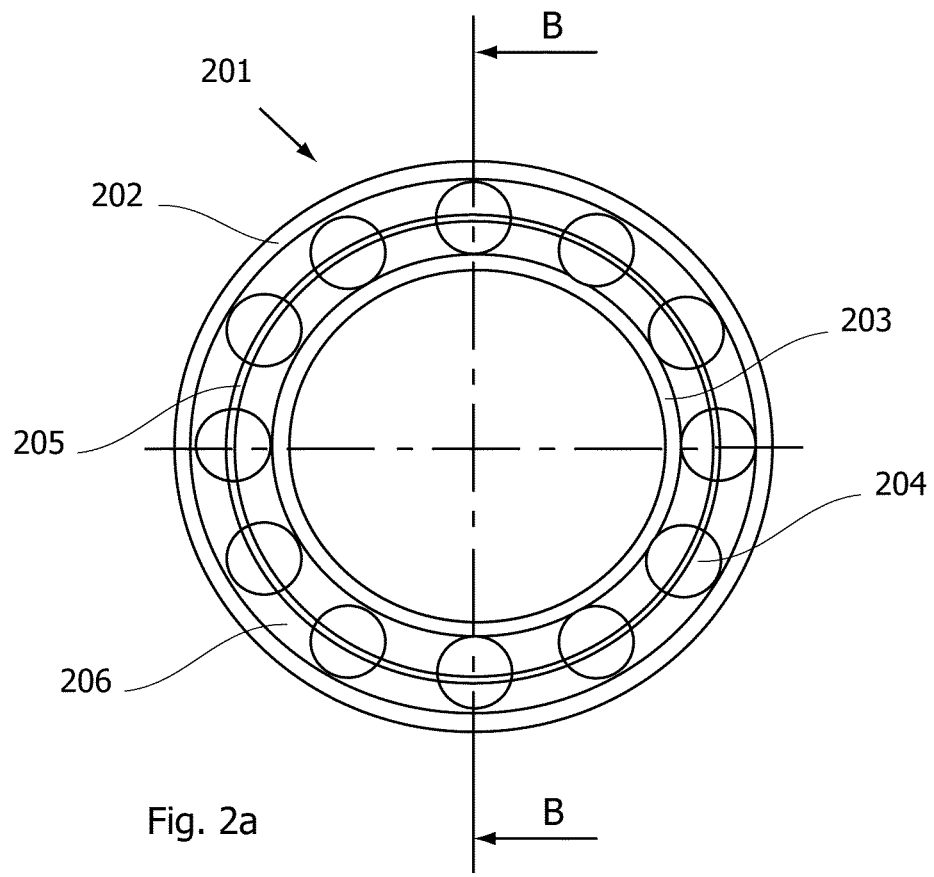
Figure 2B:
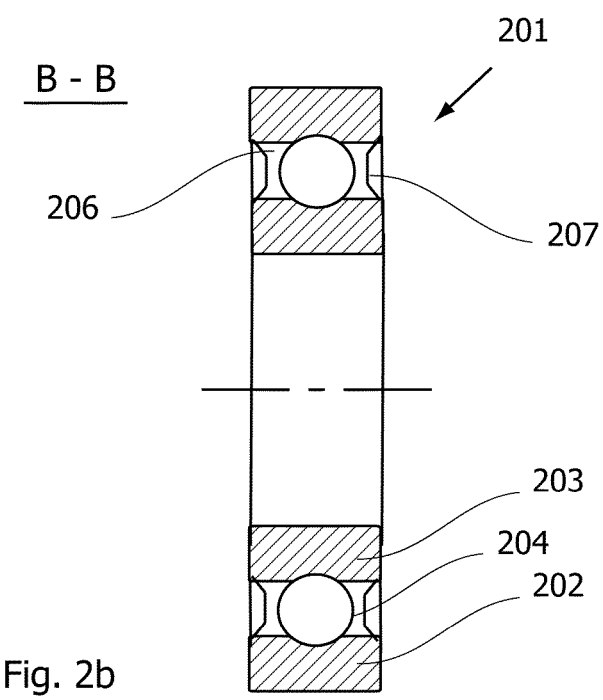

The figures show the following:

FIG. 1*a* a longitudinal section through a roller hearth furnace;

FIG. 1*b* a cross sectional view of the roller hearth furnace;

FIG. 2*a* a ball bearing;

FIG. 2*b* a sectional view B-B of the ball bearing; and

Figure 3:
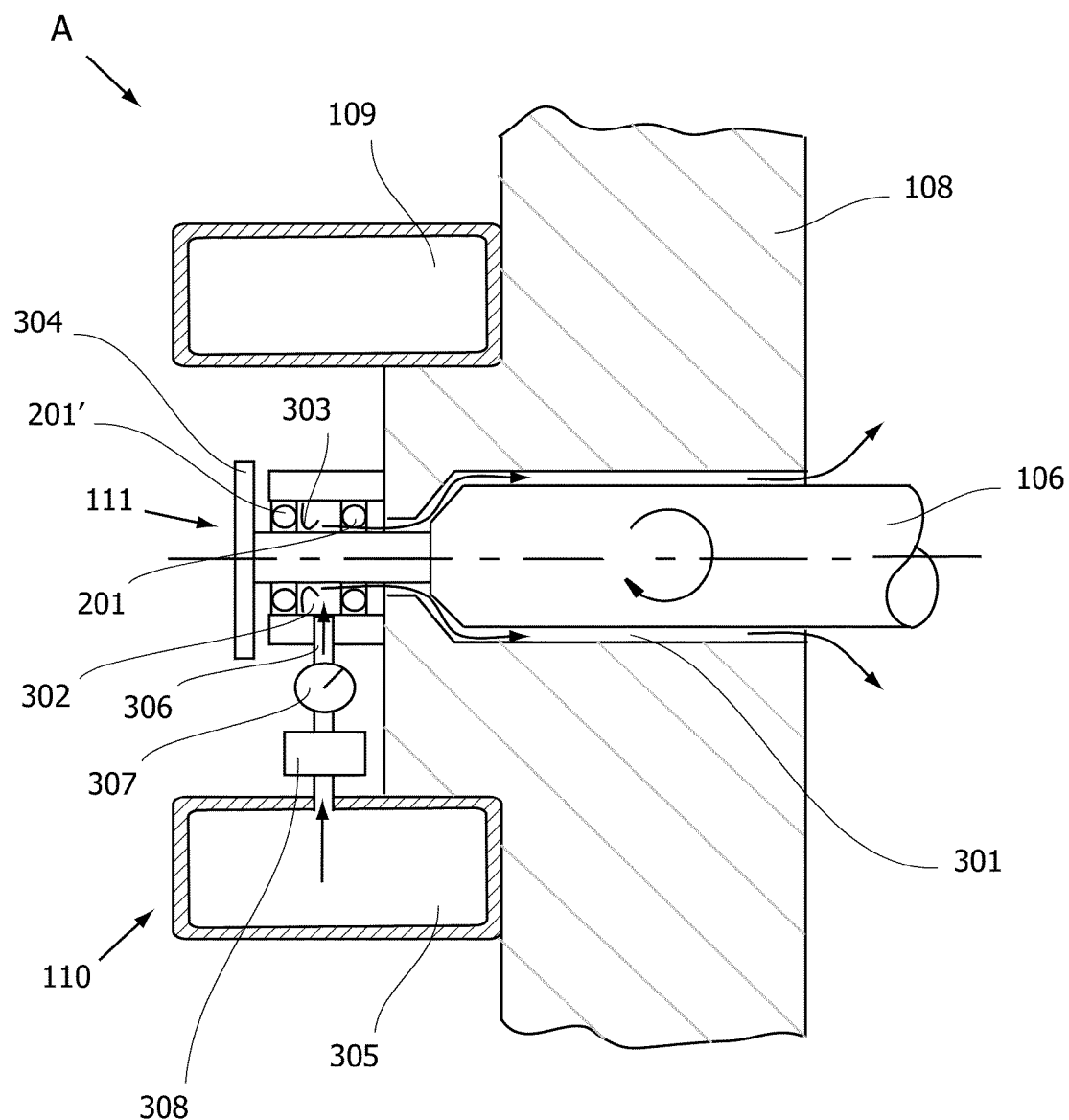

FIG. 3 a sectional view of Section A from FIG. 1*b*, with a purging system.

By way of an example, FIG. 1 schematically shows a longitudinal section through a roller hearth furnace 101 for heating a workpiece 102. The roller hearth furnace 101 comprises an elongated furnace chamber 103 that can be closed at the front and rear by height-adjustable chamber doors 104, 104', respectively. Before a workpiece 102 is placed into or taken out of the furnace chamber 103, the chamber doors 104, 104' open and, after a workpiece 102 is placed into or taken out of the furnace chamber 103, the chamber doors 104, 104' close again accordingly. These chamber doors 104, 104' can be configured, for example, as furnace slides. Even though the configuration of the roller hearth furnace 101 with chamber doors 104, 104' seems advantageous, particularly with respect to the distribution of heat in the roller hearth furnace 101, if necessary, a roller hearth furnace 101 can also be operated without chamber doors 104, 104'.

The roller hearth furnace 101 has a transport means for workpieces 102 in the form of a roller conveyor 105 that is arranged inside the furnace chamber 103 and that transports the workpiece 102 in the direction of the arrow through the roller hearth furnace 101 so as to heat the workpiece. The roller conveyor 105 is made up of several transport rollers 106 arranged one behind the other, which are driven either individually or group-wise.

Even though FIG. 1*a* only shows one workpiece 102 by way of an example, the roller conveyor 105 can also be used to transport several workpieces 102 through the roller hearth furnace 101 simultaneously so that they can be heated, whereby several workpieces 102 can be transported one behind the other and/or next to each other.

Appropriate heating elements 107 with which the workpieces 102 can be heated as they pass through the roller hearth furnace 101 are arranged in the furnace chamber 103. Such heating elements 107 are known from the state of the art and will not be elaborated upon in detail here. All other requisite components for operating the roller hearth furnace 101 are likewise not the subject matter of the invention and can be appropriately selected by the person skilled in the art.

By way of an example, FIG. 1*b* shows a cross sectional view of the roller hearth furnace 101. For the sake of clarity, the front furnace door 104 of the furnace chamber 103 is not shown here. Both sides of the furnace chamber 103 of the roller hearth furnace 101 have a furnace wall 108, 108' that serves to laterally delimit the furnace chamber 103.

On the outside of the two furnace walls 108, 108' of the furnace chamber 103, there is a stabilizer 109 for mechanically stabilizing the furnace chamber 103. This mechanical stabilization is necessary since the material of the furnace walls 108, 108' is subjected to large thermal loads due to the high temperature differences that at times occur between the interior of the furnace chamber 103 and its surroundings, which can cause deformations of the furnace walls 108, 108'. Even though only one stabilizer 109 is shown here by way of an example, it is also possible to install several stabilizers 109 in order to increase the stabilization effect on the outside of the two furnace walls 108, 108'.

Moreover, on the outside of the two furnace walls 108, 108', there is a purging system 110 for purging the roller bearing unit 111 that is likewise located there. The structure and mode of operation of the purging system 110 for the roller bearing unit 111 will be explained in greater detail in the following section pertaining to FIG. 3 on the basis of an enlarged image of Section A from FIG. 1*b*.

The roller bearing unit 111 on the outside of the two furnace walls 108, 108' of the furnace chamber 103 serves to accommodate and support one of the two ends of the individual rollers 106 of the roller conveyor 105. In order for the rollers 106 to be supported in the roller bearing units 111 outside of the furnace chamber 103, the furnace walls 108, 108' have openings (not shown here) through which the individual rollers 106 can each be guided out of the furnace chamber 103 to the outside and into the appertaining roller bearing unit 111.

Roller bearings 201 constitute an integral part of the roller bearing units 111 so that the individual rollers 106 can be accommodated and supported on both sides. By way of an example, FIG. 2*a* schematically shows such a roller bearing 201 for a roller bearing unit 111. The roller bearing 201 here is configured as a ball bearing having an outer ring 202 and an inner ring 203 between which there are individual balls 204 as the ball bearing elements, which can execute rolling movements between the outer ring 202 and the inner ring 203. In this context, the balls 204 are normally positioned and held between the outer ring 202 and the inner ring 203 by means of a ball cage 205. However, there are also versions of ball bearings 201 without a ball cage 205. Cavities filled with a lubricant 206 are formed between the individual balls 204.

This lubricant 206 especially has the function of reducing the friction that occurs between the balls 204 and the two rings 202, 203 during the rolling movements of the balls 204, thus minimizing the power dissipation as well as the wear and tear of the roller bearing 201. Suitable lubricants 206 for this are all known lubricants and greases that are normally used in roller bearings.

FIG. 2*b* schematically shows a sectional view WB through the ball bearing 201. In addition, the ball bearing 201 has a stationary seal ring 207 on both sides, and this stationary seal ring 207 protects the inside of the ball bearing against the penetration of dirt or moisture and, at the same time, prevents leakage of lubricant 206. Particularly as a function of the envisaged use of the ball bearings 201 and of the resulting requirements regarding protection against splashing water or dust, stationary seal rings 207 made of different materials are known, for instance, rubber for splashing-water protection or sheet steel for dust protection. Various types of plastic or composite materials can also be used for the stationary seal rings 207.

The type of ball bearing 201 is determined by the material of the stationary seal rings 207 in conjunction with the number of stationary seal rings 207. Aside from other combinations, the following ball bearing types find widespread use:

- ball bearings with one stationary seal ring as protection against splashing water—R type
- ball bearings with two stationary seal rings as protection against splashing water—RR or 2R type
- ball bearings with one stationary seal ring as protection against dust—Z type
- ball bearings with two stationary seal rings as protection against dust—ZZ or 2Z type The ball bearings 201 of the roller bearing units 111 serve, on the one hand, to accommodate and support the rollers 106 of the roller conveyor 105 outside of the furnace chamber 103 and, on the other hand, allow a rolling movement of the rollers 106 inside the furnace chamber 103 which, in turn, is responsible for the transport of the workpiece 102 through the roller hearth furnace 101.

Although the use of ball bearings 201 seems advantageous for supporting the rollers 106, other roller bearings such as, for instance, cylindrical roller bearings, tapered roller bearings or other roller bearings can also be employed.

Due to the arrangement of the roller bearing units 111 on the outsides of the furnace walls 108, 108', the thermal and mechanical loads on the ball bearings 201 are very high. This, in turn, causes great wear and tear of the ball bearings 201, so that, as the wear of the ball bearings 201 increases, the rolling behavior of the rollers 106 can change from easy to difficult, and possibly all the way to a complete blockage of the rollers 106. The use of the purging system 110 reduces the wear and tear.

FIG. 3 schematically shows an enlarged section of view A from FIG. 1*b*, showing part of a furnace wall 108 and part of a roller 106 as well as a stabilizer 109, a purging system 110 and a roller bearing unit 111.

Since the roller 106 is supported outside of the furnace chamber 103, an opening 301 is created in the furnace wall 108 through which the roller 106 is guided from the furnace chamber 103 to the outside and into the appertaining roller bearing unit 111. The roller 106 is supported in the roller bearing unit 111 by means of a ball-bearing pair consisting of an inner ball bearing 201 and an outer ball bearing 201'. In this context, the inner ball bearing 201 of the ball-bearing pair is arranged closer to the furnace wall 108 than the outer ball bearing 201', and both ball bearings 201 and 201' are arranged next to each other in such a way that a cavity 302 is formed between them. Both ball bearings 201 and 201' are of the ZZ type, in other words, they have two stationary seal rings 207 as protection against dust.

There is a sealing element 303 inside the cavity 302 on the side of the outer ball bearing 201' which faces the cavity 302. Since the stationary seal rings 207 of the outer ball bearing 201' are only configured as dust protection, it is the task of the sealing element 303 to seal off the cavity 302 in such a manner that no purge gas from the cavity 302 can get into the outer ball bearing 201'. For this purpose, the sealing element 303 can be configured as a rotary shaft seal, for instance, as a radial rotary shaft seal.

The outer ball bearing 201' is secured on the roller 106 by means of a retaining ring 304 that is mounted on the end of the roller 106. This retaining ring 304 is, for example, a standardized part according to DIN 471. However, other securing means can also be employed for the outer ball bearing 201'.

The purging system 110 is connected to the roller bearing unit 111. A component of this purging system 110 is a piping system 305 that is arranged below the roller bearing unit 111 and that is connected to the cavity 302 of the pair of roller bearings of the roller bearing unit 111 via a feed line 306. A flow-rate meter 307 as well as a control element 308 are integrated into the feed line 306.

Separate gas lines can be installed on the outside of the furnace wall 108 as the piping system 305 for the purge gas 305. However, pipes or housings that are already part of the construction of the roller hearth furnace 101 and that, like the already described stabilizers 109, are arranged as additional stabilizers 109 on the outside of the furnace wall 108 can also be used as the piping system 305 for the purge gas.

The feed line 306 can be, for example, configured as a flexible rubber or silicon hose. However, fixed lines made, for instance, of plastic or metal can also be installed. The selection of the material for the feed line 306 should especially take into consideration the requirements pertaining to the purge gas being used in terms of the envisaged pressure conditions and the aspect of chemical resistance.

With an eye towards easy and simple installation, the feed line 306 can be connected to the cavity 302 and to the piping system 305, for instance, by means of plug-in connections. However, other types of connections are likewise possible.

For purposes of purging the inner ball bearing 201, a conditioned purge gas is fed into the piping system 305. Depending on the type of roller hearth furnace 101, the purge gas employed can be, for example, an inert gas for furnaces with an inert-gas atmosphere or else an air flow for furnaces with air. Other gases, however, are likewise possible as the purge gas.

The purge gas is supplied to the piping system 305 at a pressure that generates a gas flow in the order of magnitude of about 10 liters per hour. The flow rate of the purge gas can be appropriately read out and monitored by means of the flow-rate meter 307. The gas flow is regulated with a control element 308 which, in the simplest case, can be a throttle or a control valve for manually setting the gas flow. As the control element 308, it is likewise conceivable to employ adjustable nozzles or orifice plates with which the flow rate of the purge gas can be influenced, for instance, by varying the shape and size of the openings of the nozzles or orifice plates. Furthermore, the possibility exists to install a complex control element 308 that allows automatic regulation of the gas flow.

The pressure applied causes the purge gas to be conveyed out of the piping system 305 via the feed line 306 and fed into the cavity 302 of the ball-bearing pair. Correspondingly, the purge gas flow flows into the inner ball bearing 201 in this process. Since the stationary seal rings 207 of the inner ball bearing 201 only provide dust protection but no gas protection, and since the construction of the inner ball bearing 201 means that it has small slits and gaps in several places, the purge gas can also flow through the inner ball bearing 201 to which it has flowed. Consequently, the purge gas penetrates from the side of the inner ball bearing 201 that is facing the cavity 302, flows through the slits and gaps into the inner ball bearing 201 and then exits once again on the side of the inner ball bearing 201 that is facing the furnace wall 108. In this process, the purge gas cannot flow simultaneously through the outer ball bearing 201' since the sealing element 303 does not allow the purge gas to flow to the outer ball bearing 201'.

After flowing through the inner ball bearing 201, the purge gas then flows further through the opening 301 in the furnace walls 108 and into the interior of furnace chamber 103. The entire flow path of the purge gas out of the piping system 305 through the feed line 306 into the cavity 302 and then further through the inner ball bearing 201 and through the opening 301 in the furnace wall 108 all the way into the furnace chamber 103 is shown accordingly by arrows.

The pressure set for the purge gas can reliably and effectively prevent furnace gas from flowing out of the furnace chamber 103 through the opening 301 and through the inner ball bearing 201. This prevents the lubricant 206 of the inner ball bearing 201 from being disintegrated by hot furnace gas. Moreover, it is also reliably prevented that the particles that are created during the rotation of the rollers 16 and that stem from the associated friction against the ceramic insulation wall of the roller hearth furnace 101 can be entrained with the furnace gas into the inner ball bearing 201. Instead, the purge gas keeps the inner ball bearing 201 free of particles since the purge gas is not contaminated. Moreover, the temperature of the purge gas is considerably lower than the temperature of the furnace gas since the latter is carried on the outside of the roller hearth furnace 101 to the roller unit 111 so that the lubricant 205 does not disintegrate, even when the gas is flowing through.

Since a roller conveyer 105 consists of many rollers 106 arranged one behind the other, the two furnace walls 108, 108' have a corresponding number of openings 301 through which the rollers 106 can be guided out of the furnace chamber 103 into the appertaining roller bearing units 111. Each of these roller bearing units 111 is characterized by a pair of roller bearings having an inner roller bearing 201 and an outer roller bearing 201' between which a cavity 302 is formed, and each of these cavities, in turn, is connected to the piping system 305 via a separate feed line 306. Here, a flow-rate meter 307 as well as a control element 308 are integrated into each separate feed line 306.

Even though the piping system 305 needs only one connection for feeding purge gas into the piping system 305—even though several connections can be provided for this purpose—it supplies a plurality of inner ball bearings 201 with purge gas, thus ensuring a corresponding reduction of the wear and tear of all of the inner ball bearings 201.

For purposes of monitoring the tightness of the individual roller bearing units 111 and thus for monitoring the function of the purging system 110, another sealing element 303 can be arranged inside the cavities 302 of the individual roller bearing units 111 in such a way that a chamber is formed. A pressure monitoring unit connected to this chamber then allows the pressure in the chamber to be monitored so that the roller bearing unit 111 can be appropriately replaced when a pressure drop is registered in this chamber.

LIST OF REFERENCE NUMERALS

101 roller hearth furnace
102 workpiece
103 furnace chamber
104, 104' furnace door
105 roller conveyor
106 transport roller, roller
107 heating element
108, 108' furnace wall
109 stabilizer
110 purging system
111 roller bearing unit
201 roller bearing/ball bearing, inner roller bearing/ball bearing
201' roller bearing/ball bearing, outer roller bearing/ball bearing
202 outer ring
203 inner ring
204 ball
205 ball cage
206 lubricant
207 stationary seal ring
301 opening
302 cavity
303 sealing element
304 retaining ring
305 piping system
306 feed line
307 flow-rate meter
308 control element

The invention claimed is:

1. A roller hearth furnace for heating workpieces, comprising at least one furnace chamber for accommodating the workpieces, said chamber having at least two furnace side walls whereby at least one transport roller for transporting the workpieces through the furnace chamber is arranged inside the furnace chamber, and whereby the furnace side walls each have at least one opening through which the transport roller can be guided, and whereby there is at least one roller bearing unit that is arranged on the outside of the furnace side walls and that is designed to accommodate and support the transport roller outside of the furnace chamber, the roller hearth furnace having a purging system for the roller bearing unit that is designed to feed a purge gas through the roller bearing unit, whereby the purge gas can be fed from one side of the roller bearing unit facing away from one of the furnace side walls through the roller bearing unit and through the opening in the other furnace side wall all the way into the furnace chamber of the roller hearth furnace, and whereby the purge gas can be provided at a pressure that is greater than the internal pressure in the furnace chamber of the roller hearth furnace, and the purging system comprises a piping system to feed the purge gas to the roller bearing unit, and the piping system is arranged on the outside of at least one of the furnace side walls, of the roller hearth furnace, wherein the roller bearing unit comprises an inner roller bearing next to which an outer roller bearing is arranged in such a way that the two roller bearings form a pair, whereby the inner roller bearing is situated closer to the outside of at least one of the furnace side walls of the roller hearth furnace than the outer roller bearing, and in that a cavity is formed between the two roller bearings of the pair of roller bearings.

2. The roller hearth furnace according to claim 1, wherein a stabilizer of the furnace wall can be employed as the piping system.

3. The roller hearth furnace according to claim 1, wherein a sealing element is arranged on one side of the outer roller bearing and this one side faces the cavity formed between the two roller bearings of the pair of roller bearings.

4. The roller hearth furnace according to claim 1, wherein the piping system of the purging system is connected to the cavity in such a way that purge gas can be fed into the cavity, whereby the purge gas can then be conveyed out of this cavity through the inner roller bearing and through the opening in the furnace side walls all the way into the furnace chamber of the roller hearth.

5. The roller hearth furnace according to claim 1, wherein the purging system has a flow-rate meter which is designed to measure the flow rate at which the purge gas can be fed through the roller bearing and through the opening in the at least one of the furnace side walls all the way into the furnace chamber of the roller hearth furnace.

6. The roller hearth furnace according to claim 1, wherein the purging system comprises a control element that is designed to regulate the flow rate of the purge gas.

7. The roller hearth furnace according to claim 1, wherein an inert gas can be employed as the purge gas.

8. The roller hearth furnace according to claims 1, wherein air that has been purified and/or dried can be used as the purge gas.

9. A method for heating workpieces in a roller hearth furnace, whereby the roller hearth furnace comprises at least one furnace chamber for accommodating the workpieces, said chamber having at least two furnace side walls whereby at least one transport roller for transporting the workpieces through the furnace chamber is arranged inside the furnace chamber, whereby the furnace walls each have at least one opening through which the transport roller is guided, and there is at least one roller bearing unit that is arranged on the outside of the furnace walls and that accommodates and supports the transport roller outside of the furnace chamber, comprising the steps of using a purging system to feed a purge gas through the roller bearing unit, whereby the purge gas is fed from one side of the roller bearing unit facing away from one of the furnace walls through the roller bearing unit and through the one furnace wall all the way into the furnace chamber of the roller hearth furnace, and whereby the purge gas is provided at a pressure that is greater than the internal pressure in the furnace chamber of the roller hearth furnace, and the purging system comprises a piping system to feed the purge gas to the roller bearing unit, and the piping system is arranged on the outside of one of the furnace walls of the roller hearth furnace, wherein the purge gas is conveyed out of a piping system of the purging system and fed into a cavity, whereby this cavity is formed between an inner roller bearing and an outer roller bearing of the roller bearing unit, and these roller bearings are arranged as a pair of roller bearings next to each other on the outside of one of the furnace walls of the furnace chamber of the roller hearth furnace in such a manner that the inner roller bearing is closer to the outside of the one furnace wall than the outer roller bearing.

\* \* \* \* \*